US006106474A

United States Patent [19]

Koger et al.

[11] Patent Number: 6,106,474

[45] Date of Patent: Aug. 22, 2000

[54] AEROGEL BACKED ULTRASOUND TRANSDUCER

[75] Inventors: James D. Koger, Santa Cruz, Calif.; Isaac Ostrovsky, Wellesley, Mass.

[73] Assignee: Scimed Life Systems, Inc., Maple Grove, Minn.

[21] Appl. No.: 08/972,962

[22] Filed: Nov. 19, 1997

[51] Int. Cl.[7] .......................... A61B 8/14

[52] U.S. Cl. .......................... 600/459; 600/467

[58] Field of Search .......................... 600/459, 462, 600/463, 466, 467; 604/53, 96, 99–103; 29/25.35

[56] References Cited

U.S. PATENT DOCUMENTS

| | | | |
|---|---|---|---|
| 4,951,677 | 8/1990 | Crowley et al. | 128/662.06 |
| 5,059,851 | 10/1991 | Corl et al. | 310/334 |
| 5,115,814 | 5/1992 | Griffith et al. | 128/662.06 |
| 5,311,095 | 5/1994 | Smith et al. | 310/334 |
| 5,313,949 | 5/1994 | Yock | 128/662.06 |
| 5,353,798 | 10/1994 | Sieben | 128/662.06 |
| 5,749,848 | 5/1998 | Jang et al. | 604/53 |
| 5,984,871 | 11/1999 | TenHoff et al. | 600/459 |

FOREIGN PATENT DOCUMENTS

| | | | |
|---|---|---|---|
| 0 640 564 A1 | 8/1993 | European Pat. Off. | 33/158 |

OTHER PUBLICATIONS

"Jet Propulsion Laboratory," Dr. Peter Tsou, (NASA Tech Briefs, The Digest of New Technology, May 1995, vol. 19, No. 5).

*Primary Examiner*—Marvin M. Lateef
*Assistant Examiner*—Ali M. Imam
*Attorney, Agent, or Firm*—Lyon & Lyon LLP

[57] ABSTRACT

An ultrasound transducer having an acoustic backing layer made of an aerogel material is disclosed. The ultrasound transducer comprises an acoustic element for transmitting and receiving ultrasound waves. An aerogel acoustic backing layer is bonded to the back side of the acoustic element. A matching layer may be attached to the front side of the acoustic element. The ultrasound transducer may be electrically connected using electrodes directly connected to the acoustic element. Alternatively, the aerogel acoustic backing may be coated with a metalized layer or doped so that it is electrically conductive. Then, the electrodes may be connected directly to the aerogel acoustic backing.

22 Claims, 1 Drawing Sheet

AEROGEL BACKED ULTRASOUND TRANSDUCER

FIELD OF THE INVENTION

The present invention relates to ultrasound transducers, and more specifically to an aerogel backed ultrasound transducer.

BACKGROUND OF THE INVENTION

Generally, ultrasound transducers are used in ultrasound imaging devices for imaging in a wide variety of applications, especially medical diagnosis and treatment. Ultrasound imaging devices typically employ mechanisms to transmit scanning beams of ultrasound energy and to receive the reflected echoes from each scan. The detected echoes are used to generate an image which can be displayed, for example, on a monitor.

A typical ultrasound transducer comprises an acoustic element which transmits and receives ultrasound waves. The acoustic element may be made of a piezoelectric or piezostrictive material, for example. The acoustic element has a front side from which ultrasonic waves are transmitted and received, and a back side which may be bonded to an acoustic backing layer. An acoustic backing layer dampens the acoustic element to shorten the pulse length, or ringdown as it is often termed and to allow the transmission and reception in one direction. To produce this effect, the acoustic backing layer is typically made of a material having an attenuative nature. Hence, conventional materials used as a backing layer have been dense materials such as tungsten and epoxy.

A significant drawback to using a dense backing layer material is that a large amount of power consumed by the acoustic element is lost in the backing layer rather than being used to transmit ultrasound waves. If 3 dB of the transducer signal is attenuated on the backing material, the equivalent of half the power drawn by the acoustic element is lost. In other words, if the transmission efficiency of the ultrasound transducer is increased by 3 dB, the power needed to drive the transducer can be cut in half for the same signal output.

In order to reduce the amount of power lost in the backing layer, transducers having air backing layers have been used. An air backing layer reflects all the power directed out of the back side of the acoustic element toward the front side of the acoustic element. This occurs because of the impedance mismatch between the air and the acoustic element. The acoustic element may be cut to the right thickness so that the reflected ultrasound wave is in phase with an ultrasound wave originally directed to the front side of the transducer.

There are several significant disadvantages associated with an air back transducer. One is that an air back transducer has a longer ringdown time than a transducer having a dense backing layer. It is also very difficult to support an acoustic element in air.

Therefore, there is a need for an improved ultrasound transducer which provides effective damping of the acoustic element to reduce ringdown, electrically insulates the ultrasound transducer, and reduces the amount of power lost in the backing layer.

SUMMARY OF THE INVENTION

The present invention provides an ultrasound transducer employing aerogel as a backing material. Aerogels are solids with extremely porous structures. Aerogels are produced by drying wet gels while retaining the spatial structure of the solid which originally contained water or solvent. Aerogels are discussed generally in "Resource Report: Jet Propulsion Laboratory," *NASA TechBriefs*, Vol. 19, No. 5, May 1995, at 8, 14. The properties and production of aerogels are described in detail in European Patent No. EP 0 640 564 A1 to Gerlach et al. Gerlach et al. suggests aerogels for use as acoustic matching layers on ultrasonic transducers. These and all other references cited herein are expressly incorporated by reference as if fully set forth in their entirety herein.

Aerogels have the lowest known density of all solid materials. Aerogels have densities as low as 0.015 g/cm$^3$. Aerogels also have sufficient strength to provide support structure for the acoustic element. In addition, aerogels provide excellent electrical isolation from the rest of the structure.

The ultrasound transducer of the present invention comprises a conventional acoustic element. For instance, the acoustic element may be a piezoelectric or piezostrictive material. An acoustic backing material made of an aerogel material is attached to a back side of the acoustic element.

Before attaching the aerogel backing material to the acoustic element, the aerogel backing material may be coated with a metalized layer so that it is electrically conductive. This allows at least one of the electrical connections to the transducer to be made to the backing material. Otherwise, electrodes must be attached directly to the acoustic element which is a more difficult assembly.

The extremely low density aerogel has a lower acoustic impedance than conventional backing materials, such as tungsten and epoxy, and a lower acoustic impedance than the acoustic element. The mismatch of acoustic impedance between the aerogel backing material and the acoustic element causes ultrasound waves to reflect back towards the front side of the transducer. Therefore, the aerogel backing material provides a transducer with a higher signal output than a transducer employing conventional backing materials. The thickness of the acoustic element is sized such that the reflected ultrasound wave is in phase and additive to the ultrasound wave initially directed toward the front side of the transducer.

The electrical insulating quality of the aerogel provides exceptionally high electrical resistance. The acoustic properties of aerogel isolate the element from internal reverberation and increase the transducer's output. Increasing the transducer signal increases signal-to-noise ratio and improves the displayed image.

A matching layer may be attached to the front side of the acoustic element. The acoustic matching layer can be tuned to dampen ringdown in order to lower the ringdown time yet transmit most of the transducer power through the matching layer. The tradeoff for reduction of the ringdown time improves axial resolution.

DETAILED DESCRIPTION OF THE INVENTION

Figure 1:
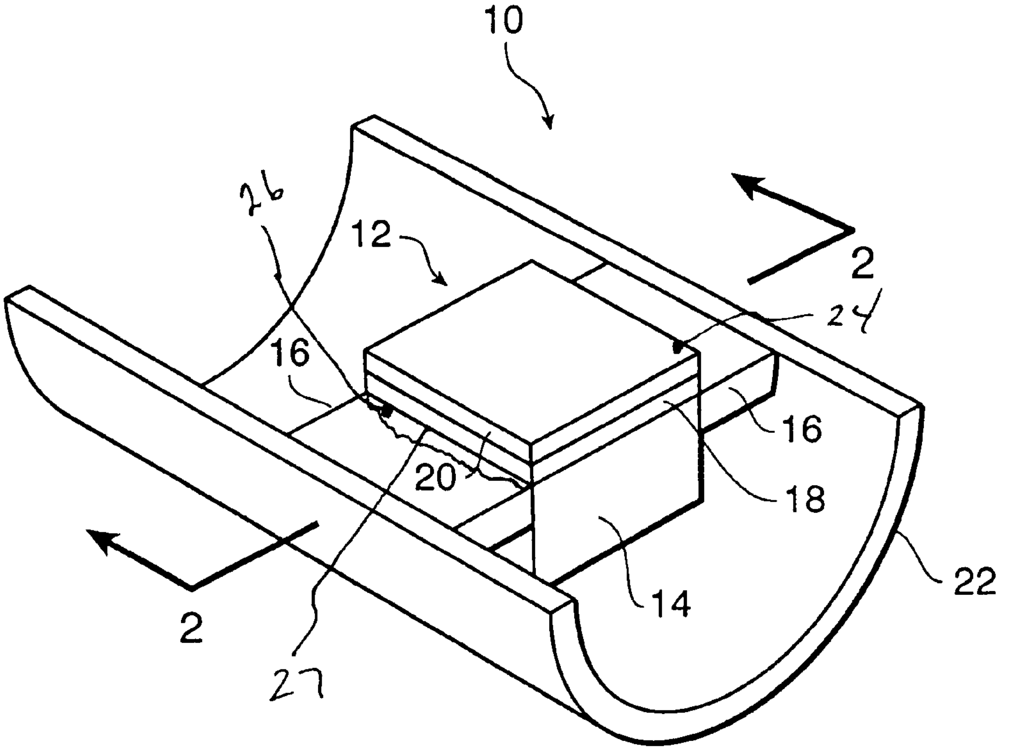
FIG. 1 is a perspective view of an ultrasound transducer in accordance with the present invention.

Referring to FIG. 1, an ultrasound transducer 12 according to the present invention is depicted. The ultrasound transducer 12 comprises an acoustic element 18. The acoustic element 18 may be a piezoelectric, piezostrictive or other suitable material depending on the transducer application. The selection of the material of the acoustic element 18 is a design choice which is well known in the art. An acoustic backing 14 made of an aerogel material is attached to a back side of the acoustic element 18.

Figure 2:
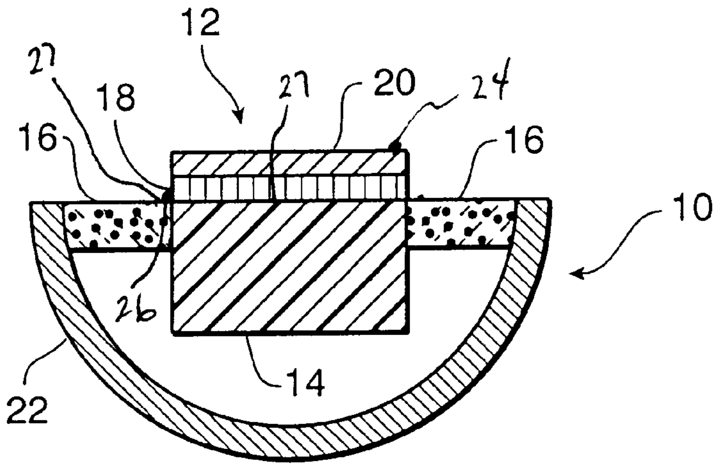
FIG. 2 is a cross-sectional view of the ultrasound transducer of FIG. 1.

An acoustic matching layer 20 may be attached to, or formed on, the front side of the acoustic element 18. The proper acoustic impedance and thickness of the acoustic matching layer 20 depends upon the environment or medium in which the ultrasound transducer 12 is used and the properties of the object to be imaged. The acoustic matching layer 20 may also be tuned to reduce ringdown while at the same time transmitting most of the power through the matching layer 20. The proper design of these parameters is known in the art. The acoustic matching layer 20 may be flat as shown in FIGS. 1 and 2, or alternatively may be curved to act as a lens to focus the ultrasound transducer 12.

For installing the ultrasound transducer 12 into an imaging device such as an imaging catheter, the ultrasound transducer 12 is mounted in a housing or support structure 22. The support structure 22 may be a semi-cylinder as shown in FIGS. 1 and 2 so that it is easily fitted into a tubular catheter or other lumen. The shape of the support structure 22 may be changed to match any particular application of the ultrasound transducer 12. The ultrasound transducer 12 may be attached to the support structure 22 using an insulating adhesive 16 such as epoxy. Alternative attachment methods may include welding, soldering, or conductive epoxies.

The ultrasound transducer 12 may be electrically connected using electrodes 24 and 26 directly connected to the acoustic element 18. Alternatively, the aerogel acoustic backing 14 may be coated with a metalized layer 27 or doped so that it is electrically conductive. Then, at least one of the electrodes may be connected to the aerogel acoustic backing 14.

The effectiveness of an aerogel acoustic backing 14 may be analyzed by considering it as an approximation of an air backing material. This approximation is supported by the following comparisons. The acoustic impedance of a material is defined as the density of the material multiplied by the speed of sound through the material, or:

acoustic impedance=Z=density×velocity$_{(sound\ in\ the\ material)}$

The densities of the relevant materials are:

| | |
|---|---|
| aerogel | 15 $kg/m^3$ |
| air (20° C.) | 1.2 $kg/m^3$ |
| common piezoelectric material (PZT) | 7500–7800 $kg/m^3$ |

Comparing these densities, it can be seen that the density of aerogel is about a factor of 10 greater than air, and PZT is 500 times denser than aerogel. Because aerogel is closer to air in density than any known solid material, and because the speed of sound through a material tends to decrease with decreasing density, the acoustic impedance of aerogel may be assumed to approximate the acoustic impedance of air.

For comparison purposes, a transducer backed with a conventional backing material having an acoustic impedance of 10 megarayles will be examined (10 megarayles is within the range of acoustic impedance for many conventional backing materials). Assuming an acoustic element consisting of the piezoelectric lead zirconium titanate material (PZT) having an acoustic impedance of 33.7 megarayles, then the mismatch in acoustic impedance between the acoustic element and the backing is:

$$\frac{Z_{PZT}-Z_{backing}}{Z_{PZT}+Z_{backing}}=\frac{33.7-10}{33.7+10}=.547$$

Air has an acoustic impedance at 10° C. of 0.000411 megarayles. Then, the mismatch acoustic impedance between the acoustic element and an air backing material is:

$$\frac{Z_{PZT}-Z_{air}}{Z_{PZT}+Z_{air}}=\frac{33.7-0.000411}{33.7+0.000411}\approx\frac{33.7}{33.7}=1$$

From the above equation, it can be seen that, even if the acoustic impedance of aerogel is greater than that of air by a factor of 10, the mismatch in acoustic impedance between the PZT and an aerogel backing material will be approximately 1. Now, comparing the aerogel (acoustic impedance approximated as air) backed transducer to the conventional material (acoustic impedance=10 megarayles) backed transducer, the difference in output may be represented as:

$$\log\frac{.547}{1}\times 20=5.3\text{dB}$$

Therefore, the aerogel backed transducer results in approximately 5.3 dB higher output than the transducer having an acoustic backing material with an acoustic impedance of 10 megarayles.

Aerogel, therefore, may provide a thinner backing because it is using primarily the acoustic impedance mismatch to increase the transducer output. In other words, the interface between the transducer acoustic element 18 and the backing material 14 creates the output difference. The increased output of the transducer having an aerogel acoustic backing 14 allows a thinner layer of backing material than conventional materials. As a result, the transducer assembly 12 may be smaller.

Thus, the reader will see that the present invention provides an improved ultrasound transducer. While the above description contains many specificities, these should not be construed as limitations on the scope of the invention, but rather as an exemplification of particular embodiments thereof. Many other variations are possible.

Accordingly, the scope of the present invention should be determined not by the embodiments illustrated above, but by the appended claims and their legal equivalents.

What is claimed is:

1. An ultrasound transducer comprising:

an acoustic element for transmitting and receiving ultrasound waves;

an acoustic backing material attached to a back side of said acoustic element, said acoustic backing layer made of an aerogel material, said aerogel material including an electrically conductive, metalized layer on a portion of said acoustic backing material, the electrically conductive, metalized layer being sandwiched between said acoustic element and said acoustic backing material, wherein the portion of aerogel material not covered by the electrically conductive, metalized layer is electrically non-conductive.

2. The ultrasound transducer of claim 1 wherein said acoustic unit includes a matching layer attached to a front side of said acoustic element.

3. The ultrasound transducer of claim 1 further comprising electronic leads operatively coupled to the acoustic element.

4. The ultrasound transducer of claim 3 wherein the leads are coaxial.

5. The ultrasound transducer of claim 3 wherein at least one lead is attached to the acoustic element.

6. The ultrasound transducer of claim 1 further comprising at least one electronic lead attached to the backing material.

7. An ultrasound transducer as defined in claim 1, the ultrasound transducer being positionable within an intravascular ultrasound imaging catheter, the catheter comprising a flexible elongate tubular member having a proximal end, a distal end, and a lumen therebetween wherein the ultrasound transducer is disposed within the distal region of said flexible elongate tubular member.

8. An ultrasound transducer of claim 1, wherein the ultrasound transducer is disposed within an imaging guidewire.

9. An intravascular ultrasound imaging catheter comprising:

a flexible, elongate tubular member having a proximal end, a distal end, and at least one lumen therebetween;

a housing for holding an ultrasound transducer, said housing being axially moveable within said at least one lumen;

an ultrasound transducer fixedly secured to said housing, said ultrasound transducer having a front surface and a back surface; and an aerogel material disposed adjacent to the back surface of the ultrasound transducer and in between said ultrasound transducer and said housing, wherein said aerogel material increases the output of said ultrasound transducer, and wherein said aerogel material electrically isolates said ultrasonic transducer to increase the signal-to-noise ratio of the imaging catheter.

10. An intravascular ultrasound imaging catheter according to claim 9, wherein the aerogel material further includes an electrically conductive, metalized layer on a portion thereof.

11. An intravascular ultrasound imaging catheter according to claim 10, further comprising at least one electrode disposed on a portion of the aerogel material including the electrically conductive, metalized layer.

12. An intravascular ultrasound imaging catheter according to claim 9, further comprising at least one electrode connected to said ultrasound transducer.

13. An intravascular ultrasound imaging catheter according to claim 9, wherein a portion of the aerogel material is doped to create an electrically conductive region on said aerogel material.

14. An intravascular ultrasound imaging catheter according to claim 13, further comprising at least one electrode disposed on a portion of the electrically conductive region on said aerogel material.

15. An intravascular ultrasound imaging catheter according to claim 9, wherein the aerogel material has a thickness such that a reflected ultrasound wave is in phase and additive to an ultrasound wave initially directed away from the front surface of said ultrasound transducer.

16. An intravascular ultrasound imaging catheter according to claim 9, further comprising a matching layer attached to the front side of said ultrasound transducer.

17. An intravascular ultrasound imaging catheter according to claim 9, wherein the ultrasound transducer is attached to the housing with an insulating epoxy.

18. An intravascular ultrasound imaging catheter according to claim 9, wherein the ultrasound transducer is attached to the housing with a weld.

19. An intravascular ultrasound imaging catheter according to claim 9, wherein the ultrasound transducer is attached to the housing with a solder.

20. A method of forming an ultrasound transducer for use with an intravascular ultrasound imaging catheter, comprising the steps of:

depositing a conductive metal on an aerogel material;

affixing the aerogel material to a back side of the ultrasound transducer;

mounting at least one electrode to the aerogel material, said electrode contacting the conductive metal on the aerogel material; and affixing the ultrasound transducer and aerogel material to a housing.

21. A method according to claim 20, wherein the conductive metal is deposited on the aerogel material in a metallic layer.

22. A method according to claim 20, wherein the conductive metal is deposited on the aerogel material by doping.

* * * * *